United States Patent [19]
den Dulk

[11] Patent Number: 5,383,910
[45] Date of Patent: Jan. 24, 1995

[54] METHOD AND APPARATUS FOR TACHYARRHYTHMIA DETECTION AND TREATMENT

[75] Inventor: Karel den Dulk, Maastricht, Netherlands

[73] Assignee: Medtronic, Inc., Minneapolis, Minn.

[21] Appl. No.: 19,511

[22] Filed: Feb. 19, 1993

[51] Int. Cl.⁶ ............................................. A61N 1/368
[52] U.S. Cl. .................................. 607/14; 128/705; 128/706
[58] Field of Search ................... 128/705, 706; 607/14

[56] References Cited

U.S. PATENT DOCUMENTS

| | | | |
|---|---|---|---|
| 4,572,192 | 2/1986 | Jackman et al. | 607/14 |
| 4,860,749 | 8/1989 | Lehmann . | |
| 5,107,850 | 4/1992 | Olive | 128/705 |
| 5,205,283 | 4/1993 | Olson | 607/14 |

OTHER PUBLICATIONS

"Automatic Tachycardia Recognition", by R. Arzbaecher et al., PACE, May-Jun., 1984, pp. 541-547.

"Necessity of Signal Processing in Tachycardia Detection" in *The Third Decade of Cardiac Pacing: Advances in Technology in Clinical Applications*, by Furman et al. Futura Publications, 1982, pp. 265-274, Part III, Chapter 1.

"MATIC-An Intracardiac Tachycardia Classification System", by Leong et al., PACE, vol. 15, 1992, 1317-1331.

"Antitachycardia Pacing: Is There a Universal Pacing Mode to Terminate Supraventricular Tachycardia?", den Dulk et al., in Cardiac Arrhythmias, Chapter 16, edited by Brugada, et al. 1987.

"Is There a Universal Antitachycardia Pacing Mode?", den Dulk et al., American Journal of Cardiology, vol. 57, pp. 950-955.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

A device for detection and treatment of tachycardias, which is able to selectively identify the occurrence of re-entrant AV nodal tachycardia, and to distinguish it from sinus tachycardias. The apparatus monitors the occurrence of atrial and ventricular depolarizations during a detected tachycardia, and, in the event that a series of ventricular depolarizations occur which are each closely preceded or closely followed by an atrial depolarization, at an interval substantially less than would be expected in the case of a sinus tachycardia, re-entrant AV nodal tachycardia is identified, and an appropriate therapy regimen is triggered.

8 Claims, 3 Drawing Sheets

METHOD AND APPARATUS FOR TACHYARRHYTHMIA DETECTION AND TREATMENT

BACKGROUND OF THE INVENTION

This invention relates to automatic implantable devices to detect and differentiate between tachycardias (rapid heart rhythms) for diagnostic purposes or in order to therapeutically stimulate the heart. The invention relates more specifically, to devices which analyze the rhythm of both the atrium and ventricle in order to distinguish among tachycardias and have the capability of treating both ventricular and supraventricular tachyarrhythmias.

The article "Automatic Tachycardia Recognition" by R. Arzbaecher et al., PACE, May-June 1984, pp. 541-547, discloses an algorithm implemented in a microprocessor based implantable device employing both atrial and ventricular rate detection via separate bipolar leads in order to measure the AA and VA, or VV and AV intervals in order to distinguish among various types of tachycardias. The Arzbaecher et al. article also discloses the concept of employing a single atrial extra stimulus to distinguish sinus tachycardia from 1:1 paroxysmal tachycardia.

Other proposals for employing atrial and ventricular detection and interval comparison are set forth in *The Third Decade of Cardiac Pacing: Advances in Technology in Clinical Applications*, Part III, Chapter 1, "Necessity of Signal Processing in Tachycardia Detection" by Furman et al. (edited by S. Barold and J. Mugica, Futura Publications., 1982, pages 265-274) and in the Lehmann U.S. Pat. No. 4,860,749. In both cases, atrial and ventricular rates or intervals are compared to one another in order to distinguish sinus and pathological tachycardias.

A recent article, "MATIC—An Intracardiac Tachycardia Classification System" by Leong et al , PACE, Vol 15, September 1992, Pages 1317-1331, disclosed an automated tachycardia analysis system which employs a neural network for morphology analysis and which compares measured A-V intervals to measured V-V intervals for classification of tachycardias displaying 1:1 correspondence between atrial and ventricular depolarizations.

SUMMARY OF THE INVENTION

In the context of an automatic implantable device for diagnosing or diagnosing and treating tachyarrhythmias, the present invention comprises a method and apparatus for distinguishing AV nodal reentrant tachycardias from other tachycardias which exhibit 1:1 correspondence between atrial and ventricular rhythms. The apparatus is provided with means for sensing the atrial electrocardiogram and the ventricular electrocardiograms, for deriving atrial and ventricular cycle lengths (ACL's and VCL's, respectively) from the respective atrial and ventricular electrocardiograms and for determining whether the ventricular cycle lengths (and optionally the atrial cycle lengths) reflect a ventricular and/or atrial rate exceeding a preset tachycardia rate threshold.

If the ventricular rate (or optionally the atrial rate) indicates the presence of a tachycardia, the device determines whether closely spaced atrial and ventricular depolarizations, in either order, occur sequentially within a series of heart cycles. In the context of the invention, atrial and ventricular depolarizations are considered to be indicative of reentrant AV nodal tachycardia if they are within a short, defined time interval less than would be expected in a sinus tachycardia which occurs at a rate which meets the criteria for tachycardia detection. This defined time interval may be, for example, up to 50-100 ms, with intervals of 50 ms or less preferred. A series of a predetermined number of successive, closely spaced atrial and ventricular depolarizations results in a diagnosis of AV nodal reentrant tachycardia.

If AV nodal reentrant tachycardia is diagnosed, a therapy particularly adapted to terminate such an arrhythmia is delivered. The preferred therapy for treating AV nodal reentrant tachycardia is pacing the atrium using universal mode anti-tachycardia pacing, as described in Chapter 16 of *Cardiac Arrhythmias*, edited by Brugada et al., 1987, entitled "Antitachycardia pacing: Is there a Universal Pacing Mode to Terminate Supraventricular Tachycardia?", den Dulk, et al. and in the article "Is there a Universal Antitachycardia Pacing Mode?", den Dulk et al., American Journal of Cardiology, Volume 57, pages 950-955, 1986, both of which are incorporated herein by reference in their entireties.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

Figure 1:
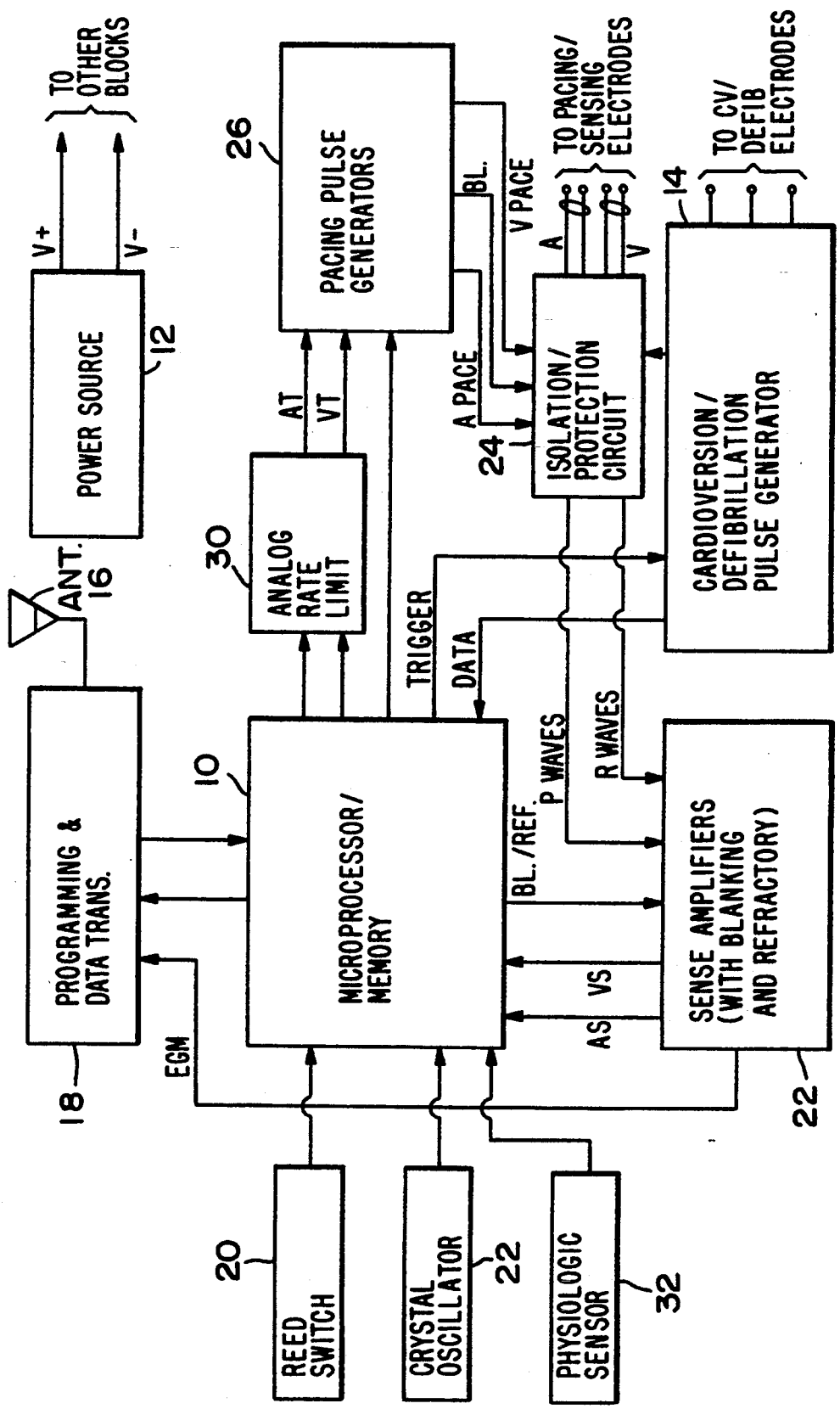
FIG. 1 is a block diagram representation of the electrical circuit of an implantable device in which the inventive detection and treatment method may be embodied.

FIG. 1 is a block diagram of the major components of automatic implantable device for detecting and treating bradycardia and tachyarrhythmias. It is contemplated that such a device would be implemented in analog and digital micro-circuits under the control of a central microprocessor/memory block 10 powered by a battery power source in block 12. The high power pulse generator block 14 would include the cardioversion/-defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art.

It is contemplated that the implantable device depicted in FIG. 1 would function under the control of a resident operating program or software retained in memory within the microprocessor/control/memory block 10 and would be programmable by an external programmer/receiver (not illustrated in FIG. 1) communicating with the implanted device by radio frequency energy received or transmitted by antenna 16 under the control of the programming and data transmission block 18 and reed switch 20 which is responsive to an external magnet. The programming and data transmitting block 18 would be capable of receiving programming instructions and directing them to the memory within microprocessor/control/memory block 10 as well as transmitting data stored within the memory within block 10 as well as an electrogram representing the patient's atrial and ventricular activity in a manner well known in the pacing art.

For purposes of implementing the present invention, stored A-A, A-V, V-A and V-V intervals may be stored in portions of the memory within block 10 configured as circular buffers, such that at any given time, stored intervals indicative of the heart rhythm during at least the preceding several minutes are available for analysis. Following onset and detection of a ventricular rate indicative of a tachyarrhythmia, stored intervals occurring after onset of tachycardia may be used in conjunction with the present invention to determine whether the detected tachycardia is an A-V nodal reentrant tachycardia.

The timing of all timing and processing functions, including the determination of atrial and ventricular cycle lengths, is controlled by counters within block 10 which measure and define time intervals under control of the microprocessor in block 10 and are driven by crystal oscillator 22 in a manner well known in the prior art of implantable digital pacemakers. The remaining blocks of FIG. 1 include the isolation/protection or interface block 24 which operates to direct atrial and ventricular pacing stimuli from the pacing pulse generator block 26 to respective atrial and ventricular output terminals which in turn are coupled through pacing leads to bipolar pacing electrodes situated in or near the atrium and ventricle of the heart, respectively. In addition, the interface 24 (when unblanked) couples the atrial and ventricular electrograms (or P-waves and R-waves respectively) to the sense amplifier block 28. Interface 24 is blanked or prevented from passing any signals picked up on the bipolar atrial and ventricular pacing/sensing electrodes to the sense amplifier block 28 during short blanking intervals following the delivery of an atrial or ventricular pacing stimulus in a fashion well known in the pacing art.

Furthermore, the interface 24 disconnects or shorts out the pacing/sensing electrodes during the delivery and for a short period after the delivery of a cardioversion/defibrillation shock by application of a control signal to the interface 24 by the cardioversion/defibrillation pulse generator block 14.

The P-waves and R-waves transmitted through the interface 24 to the sense amplifiers 28 are amplified and shaped to generate atrial and ventricular signals AS and VS, respectively, which are conducted to block 10 in order to derive the atrial and ventricular cycle lengths, the A-V and V-A intervals, and other intervals which may be appropriate to the overall function of the device. A further signal from a physiologic sensor 32 representative of cardiac or patient activity may also be applied to the block 10 in order to control the bradycardia pacing rate in the DDDR or other rate responsive mode of operation. The output of the sensor 32 may also be employed to augment detection and classification of tachyarrhythmias, for example to assist in differentiating sinus tachycardias from pathological rhythms.

The microprocessor within block 10 responds to atrial and ventricular AS and VS signals and to the generation of atrial and ventricular pacing pulses by defining appropriate atrial and ventricular refractory and blanking intervals which are in turn communicated to the sense amplifier block 28 during certain windows of time following each respective AS and VS and following each pacing pulse in a fashion well known in the pacing art.

It is contemplated that the system depicted in FIG. 1 may be programmed to operate in any of the known bradycardia single or dual chamber pacing modes. The signal from the physiologic sensor 32 may be employed to modify the atrial and ventricular escape intervals to allow for a certain range of atrial and ventricular pacing depending upon the level of the patient's activity in a fashion well known in the bradycardia pacing art. The atrial and ventricular escape intervals established in memory are compared against the atrial and ventricular cycle lengths encountered in the patient and, if a bradycardia condition exists, the block 10 applies atrial and ventricular pace trigger signals AT and VT through analog rate limiter block 30 to the pacing pulse generator 26 which responds by developing the respective A pace and V pace signals. Analog rate limiter 30 operates to limit atrial and ventricular pacing rates to a safe high rate into effect an appropriate upper rate behavior in the event that the spontaneous atrial rate exceeds the programmed upper rate limit in a fashion well known in the pacing art.

It is moreover contemplated that the microprocessor in block 10 may be programmed to provide a regimen of successive treatment therapies to treat any tachyarrhythmia that is not corrected to sinus rhythm by the delivery of the first therapy in the regimen. The successive therapies may be programmed to be more aggressive and may include both pacing energy and cardioversion defibrillation shock therapies.

Figure 2:
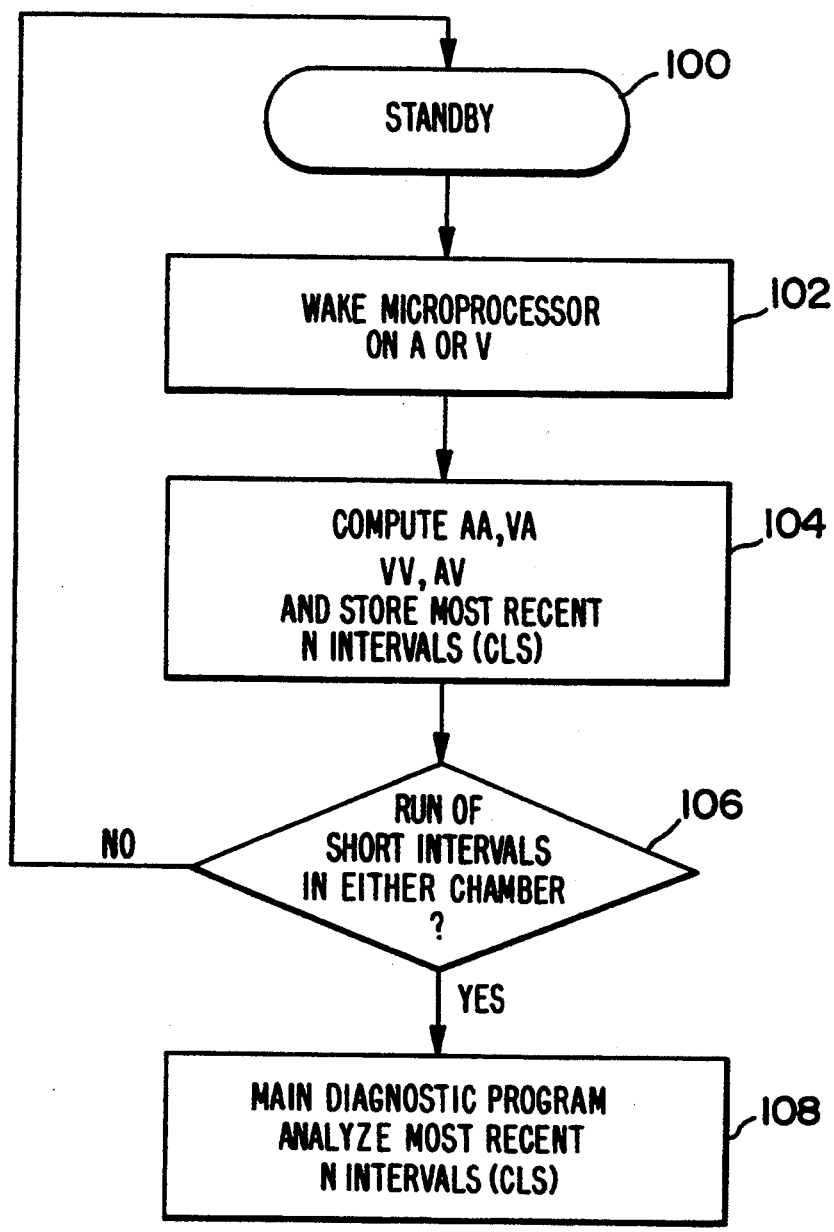
FIG. 2 is a flow chart of the main diagnostic or tachycardia detection program embodied in the device illustrated in FIG. 1.
Figure 3:
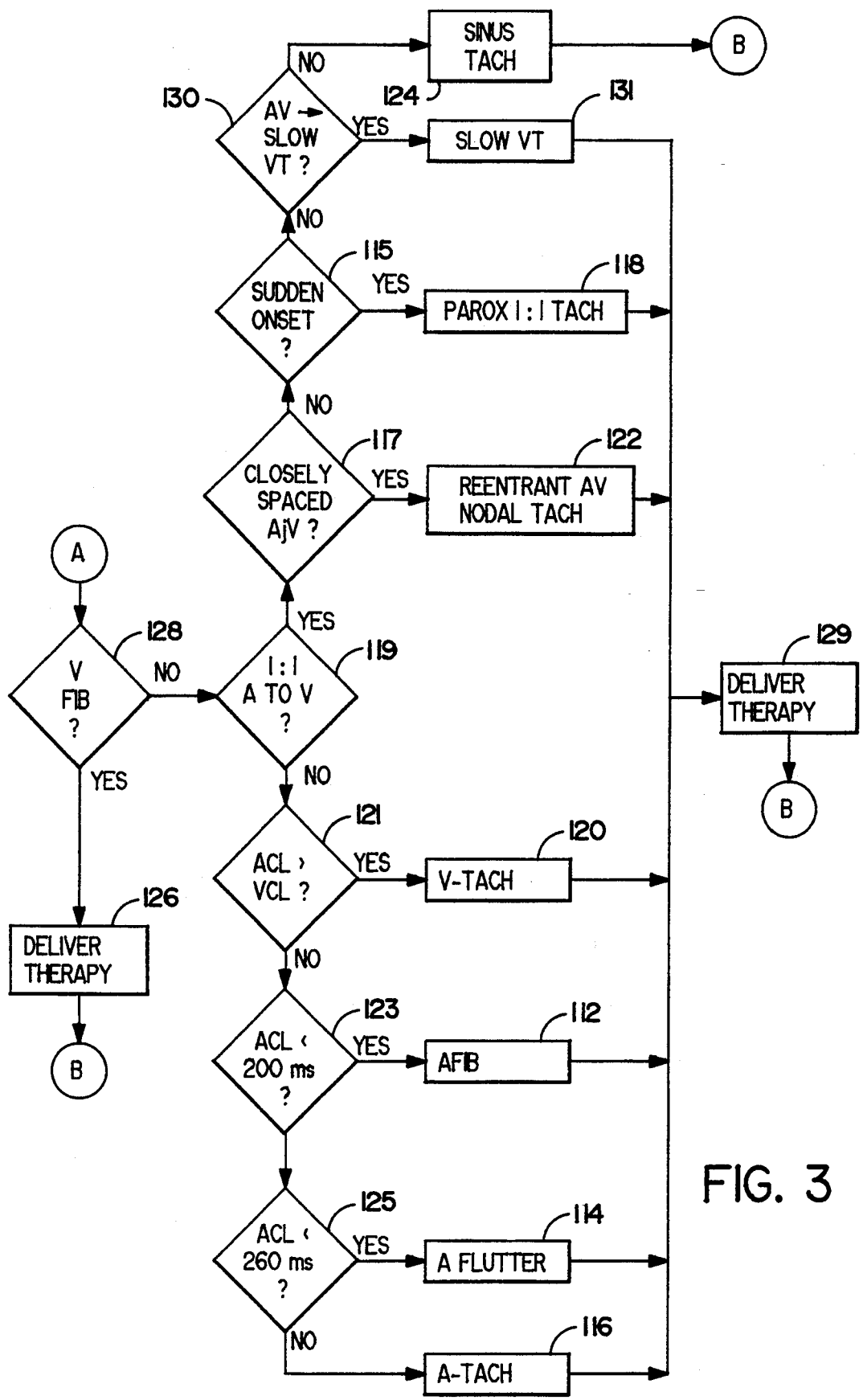
FIG. 3 is a flow chart of the tachycardia analysis function for recognizing and distinguishing AV nodal reentrant tachycardia.

The system as described is rendered operational by resident software within the memory in block 10 which is capable of distinguishing normal sinus rhythm within the acceptable upper and lower rate limits of the main bradycardia pacing routine and distinguishing various types of tachyarrhythmias in accordance with the overall program depicted in FIG. 2 and the tachycardia analysis routine depicted in FIG. 3.

FIG. 2 conforms generally to FIG. 1 of the aforementioned Arzbaecher et al. article and represents a generalized flow chart for tachycardia identification which detects a sustained fast rate in either the atrium or the ventricle and awakens the tachycardia analysis program illustrated in FIG. 3 in order to conduct a detailed analysis of the tachycardia and its immediately preceding beats. FIG. 3 includes a portion adapted from FIG. 2 of the Arzbaecher article with the addition of steps specifically addressed to identifying and treating A-V nodal reentrant tachycardia according to the present invention.

Referring to FIG. 2, it shows in block 100 the standby mode of operation of the microprocessor in order to conserve power. When an AS or VS signal is received from the sense amplifier 28 of FIG. 1, it awakens the microprocessor in step 102 to compute the AA, VA, VV and AV intervals and store the most recent series of intervals, extending over the preceding several minutes, as depicted in block 104. In the event that a predetermined number of short intervals less than the tachycardia detection interval (TDI) or fibrillation detection interval (FDI) in either chamber occurs, during a predetermined time interval or a preceding series of heart cycles, tachyarrhythmia is detected at step 106 and the tachycardia analysis program of FIG. 3 is commenced. As long as tachyarrhythmia is not detected, the overall program continues to store the most recent intervals, discarding the oldest in turn and the device operates as a demand pacemaker.

FIG. 3 illustrates the operation of the device of FIG. 1 to perform tachyarrhythmia classification and treatment including detection of reentrant AV nodal tachycardia using the present invention and corresponds to block 108 of FIG. 2. In particular, FIG. 3 is based on FIG. 2 of the above cited Arzbaecher et al. reference, with the addition of ventricular fibrillation detection and the addition of AV nodal reentrant tachycardia detection according to the present invention. The purpose of the functions illustrated is to distinguish among the tachyarrhythmias identified in blocks 112, 114, 116, 118, 120, 122, 124 and 128 and to direct the device depicted in FIG. 1 to apply the appropriate therapy or therapy regimens.

For example, atrial fibrillation (block 112), atrial flutter (block 114) would be treated by therapies including atrial cardioversion and or defibrillation shocks. However, atrial tachycardia (block 116), would be treated initially with atrial antitachycardia pacing. Paroxysmal 1:1 tachycardia (block 118) and stable ventricular tachycardia (block 120) may be treated by one or more ventricular antitachycardia pacing therapies or regimens of pacing therapies, possibly followed by a cardioversion or defibrillation therapy if the pacing therapies were unsuccessful. Atrial flutter (block 114) may in some cases also, initially be treated by means of pacing therapies. Sinus tachycardia (block 124) would be untreated as it would be considered non-pathologic in nature.

A-V nodal tachycardia, (block 122) would be treated by a pacing therapy optimized to terminate this particular arrhythmia. For example, simultaneous pacing in the atrium and ventricle at a rate in excess of the sensed ventricular rate has been effective in some patients, and burst atrial pacing has also been effective in some patients. However adaptive overdrive pacing of the atrium with an automatically increasing number of stimuli, (universal antitachycardia pacing mode) as described in above cited den Dulk, et al. references, is believed to be the preferred therapy.

A stored sequence of intervals associated with the detected tachyarrhythmia is read from the memory. This sequence of intervals (the analysis sequence) during the detected tachyarrhythmia are analyzed in block 128 to determine whether ventricular fibrillation is present. Ventricular fibrillation might be detected if a certain percentage of the most recently stored V-V intervals in the analysis sequence are less than a fibrillation detection interval (FDI) e.g. 220 ms. Alternatively, such stored ventricular intervals of less than 300 ms in conjunction with A-V dissociation, as set forth in the above cited Leong article might be used to diagnose ventricular fibrillation. If ventricular fibrillation is diagnosed, a ventricular defibrillation shock is delivered at 126.

If ventricular fibrillation is not detected, the most recently stored intervals in the analysis sequence are analyzed in block 119 to determine if there is 1:1 correspondence between sensed atrial and ventricular depolarizations. If there is 1:1 correspondence, the device checks at 117 to determine whether these most recently stored intervals are comprised of atrial and ventricular depolarizations occurring closely spaced to one another, at intervals which are less than would be expected in a sinus tachycardia, e.g. within 50–100 milliseconds of each other, irrespective of order. This time interval range (e.g. 0–50 ms or 0–100 ms) indicative of reentrant nodal tachycardia may be specified by the physician, based upon electrophysiologic studies of the patient's rhythm. Optionally, the interval range could be made variable dependant on the rate of the detected tachycardia.

As discussed above, atrial depolarizations followed closely (e.g. within 50 to 100 milliseconds) by ventricular depolarizations and ventricular depolarizations followed closely (e.g. within 50–100 milliseconds) by atrial depolarizations are considered to be indicative of reentrant AV nodal tachycardia. Detection of a series of or a predetermined number of such closely timed atrial and ventricular depolarizations results in a diagnosis of reentrant AV nodal tachycardia at 122. If reentrant AV nodal tachycardia is diagnosed at 122 a therapy optimized for A-V nodal tachycardia as discussed above is delivered at 129.

If A-V nodal tachycardia is not diagnosed, the earliest V-V intervals in the analysis sequence are analyzed at 115 to determine whether the onset of the tachycardia was gradual or sudden. For example, the first four cardiac cycles in the analysis sequence which satisfied the high rate condition may be compared to the four cardiac cycles that preceded them, and if all four have cycle lengths substantially shorter than the average of the four preceding cardiac cycles, then the tachycardia is concluded to be paroxysmal ventricular tachycardia with 1:1 retrograde conduction and pace-terminable. In such case, a ventricular pacing therapy such as autodecremental overdrive pacing or ventricular burst pacing might be applied.

In some cases it may also be possible to differentiate between sinus tachycardia and slow ventricular tachycardia with 1:1 retrograde conduction by determining whether the most recent series of A-V intervals in the analysis sequence are greater than would be expected for a sinus tachycardia at the detected rate. This function is performed at block 130, if determined to be appropriate by the physician, with the stored A-V intervals analyzed to determine whether they fall within a slow VT A-V interval range selected by the physician based on electrophysiologic testing of the patient. If so, slow VT is detected at block 131. The slow VT A-V interval range should not overlap with the A-V intervals expected for sinus tachycardia or for reentrant A-V nodal tachycardia discussed above. The Slow VT A-V interval range may vary as a function of the detected rate of the tachycardia, as discussed above in conjunction with block 117, and block 130 may optionally be activated only for slow tachycardia rates. If slow VT with 1:1 retrograde conduction is diagnosed at 131, a ventricular pacing therapy such as autodecremental overdrive pacing or ventricular burst pacing might be applied at 129. If slow VT is not detected or if block 130 is not enabled, sinus tachycardia is diagnosed at 124. Sinus tachycardia is a non-pathological heart rhythm and not treatable by anti-tachycardia pacing. Therefore, no therapy is delivered.

In the event that 1:1 correspondence is not present, atrial cycle lengths in the analysis sequence are checked at 121 to determine whether they are shorter than the corresponding ventricular cycle lengths. If so, the device compares the atrial cycle lengths against interval or rate based criteria at 123 and 125 to diagnose atrial tachycardia at 116, atrial flutter at 114 or atrial fibrillation at 112. In the event that the ventricular cycle length during the analysis sequence is shorter than the atrial cycle length, ventricular tachycardia is diagnosed at 120. Following diagnosis, an appropriate therapy as discussed above is delivered at 129.

In the event that atrial fibrillation or atrial flutter are diagnosed, the device may apply an appropriate shock between the pair of electrodes juxtaposed across the atrium of the heart. If atrial tachycardia is diagnosed, pacing therapies may be applied in an attempt to entrain or break the atrial tachycardia, and if that fails, cardioversion defibrillation shock may be delivered. As noted above, in some cases, pacing therapies might initially be attempted in cases of atrial flutter. In the event that the ventricular tachycardia is diagnosed, a ventricular antitachycardia pacing or cardioversion therapy would be delivered, depending on the rate of the tachycardia.

Although only a single proposed embodiment of the invention has been described, it will be apparent from that description to those skilled in the field to which the invention pertains, that the present invention may be employed and have value in a wide variety of embodiments.

The invention may be employed, for example, in a device which serves only as a monitoring device, without the ability to deliver therapy. Similarly, the invention may be employed in a device which treats only a subset of the arrhythmias described above, for example a device for antitachycardia pacing in the atrium only or the atrium and ventricle. In addition, while the disclosed embodiment employs electrical stimulation pulses as therapies, the invention may also be usefully employed in a device which provides another form of antiarrhythmic therapy such as delivery of an antiarrhythmic drug.

Accordingly, it is intended that the disclosed embodiment should be taken as exemplary, rather than limiting in interpreting the claims which follow. In conjunction with the above disclosure, I claim:.

I claim:

1. A method of detecting re-entrant A-V nodal tachycardia in a patient's heart comprising the steps of:
   sensing the atrium and ventricle of the patient's heart to detect atrial and ventricular depolarization signals;
   measuring the intervals between successive depolarization signals in a chamber of said patient's heart;
   measuring the time intervals between successive atrial and ventricular depolarization detection signals; and
   detecting the presence of re-entrant A-V nodal tachycardia in response to the detection of a series of depolarization signals in a said chamber of said patient's heart manifesting a rate in excess of a tachycardia rate criterion, in which successive ventricular depolarization signals are followed by atrial depolarization signals separated from said ventricular depolarization signals by intervals of time which fall within a first predetermined range of intervals substantially less than the expected duration of A-V intervals which would occur in a sinus or other tachycardia at a rate in excess of said tachycardia rate criterion.

2. A method of detecting and treating a re-entrant A-V nodal tachycardia in a patient's heart comprising the steps of:
   sensing the atrium and ventricle of the patient's heart to detect atrial and ventricular depolarization signals;
   measuring the intervals between successive depolarization signals in a chamber of said patient's heart;
   measuring the time intervals between successive atrial and ventricular depolarization signals;
   detecting the presence of re-entrant A-V nodal tachycardia in response to the detection of a series of depolarization signals in said chamber of said patient's heart manifesting a ventricular rate in excess of a tachycardia rate criterion, in which successive ventricular depolarization signals are followed by atrial depolarization signals separated from said ventricular depolarization signals by intervals of time which fall within a first predetermined range of intervals substantially less than the expected duration of A-V intervals which would occur in a sinus or other tachycardia at a rate in excess of said tachycardia rate criterion; and
   in response to detection of said re-entrant A-V nodal tachycardia, delivering a predefined antitachycardia therapy.

3. A method according to claim 1 or claim 2 wherein said detecting step comprises detecting A-V nodal re-entrant tachycardia in response to successive ventricular depolarization signals followed by atrial depolarization signals separated from said ventricular depolarization signals by intervals of time less than a predefined interval, said predefined interval being 100 milliseconds or less.

4. A method according to claim 1 or claim 2, comprising the additional step of detecting slow ventricular tachycardia with 1:1 retrograde conduction, in response to successive ventricular depolarization signals preceded by atrial depolarization signals by intervals of time within a second predetermined range of intervals greater than the expected duration of A-V intervals which would occur in a sinus tachycardia at a rate in excess of said tachycardia rate criterion.

5. Apparatus for detecting re-entrant A-V nodal tachycardia in a patient's heart, comprising:
   means for sensing the atrium and ventricle of the patient's heart to detect atrial and ventricular depolarization signals;
   first measuring means for measuring the intervals between successive depolarization signals in a chamber of said patient's heart;
   second measuring means for measuring the time intervals between successive atrial and ventricular depolarization signals; and
   detecting means, responsive to said first and second measuring means, for detecting the presence of re-entrant A-V nodal tachycardia in response to the detection of a series of depolarization signals in said chamber of said patient's heart manifesting a rate in excess of a tachycardia rate criterion, in which successive ventricular depolarization signals are followed by atrial depolarization signals separated from said ventricular depolarization signals by intervals of time which fall within a first predetermined range of intervals substantially less than the expected duration of A-V intervals which would occur in a sinus or other tachycardia at a rate in excess of said tachycardia rate criterion.

6. Apparatus for detecting and treating a re-entrant A-V nodal tachycardia in a patient's heart, comprising:

means for sensing the atrium and ventricle of the patient's heart to detect atrial and ventricular depolarization signals;

first measuring means for measuring the intervals between successive ventricular depolarization signals;

second measuring means for measuring the time intervals between successive atrial and ventricular depolarization detection signals;

detecting means, responsive to said first and second measuring means, for detecting the presence of re-entrant A-V nodal tachycardia in response to the detection of a series of depolarization signals in said chamber of said patient's heart manifesting a rate in excess of a tachycardia rate criterion, in which successive ventricular depolarization signals are followed by atrial depolarization signals separated from said ventricular depolarization signals by intervals of time which fall within a first predetermined range of intervals substantially less than the expected duration of A-V intervals which would occur in a sinus or other tachycardia at a rate in excess of said tachycardia rate criterion; and means responsive to detection of said re-entrant A-V nodal tachycardia, for delivering a predefined antitachycardia therapy.

7. An apparatus according to claim 5 or claim 6 wherein said detecting means comprises means for detecting A-V nodal re-entrant tachycardia responsive to successive ventricular depolarization signals followed by atrial depolarization signals separated from said ventricular depolarization signals by an interval of time less than a predefined interval, said predefined interval being 100 milliseconds or less.

8. An apparatus according to claim 5 or claim 6, wherein said detecting means further comprises means for detection of slow ventricular tachycardia with 1:1 retrograde conduction in response to successive ventricular depolarization signals preceded by atrial depolarization signals by intervals of time within a second predetermined range of intervals greater than the expected duration of A-V intervals which would occur in a sinus tachycardia at a rate in excess of said tachycardia rate criterion.

* * * * *